US008900610B2

(12) United States Patent
Wellinghoff

(10) Patent No.: US 8,900,610 B2
(45) Date of Patent: Dec. 2, 2014

(54) BIOCIDAL FIBROUS AND FILM MATERIALS COMPRISING SILVER AND CHLORITE IONS

(75) Inventor: Stephen T. Wellinghoff, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 906 days.

(21) Appl. No.: 11/215,738

(22) Filed: Aug. 30, 2005

(65) Prior Publication Data

US 2007/0237810 A1    Oct. 11, 2007

Related U.S. Application Data

(60) Provisional application No. 60/605,569, filed on Aug. 30, 2004.

(51) Int. Cl.
| | | |
|---|---|---|
| *A01N 59/16* | (2006.01) | |
| *A01N 59/00* | (2006.01) | |
| *A01N 25/10* | (2006.01) | |
| *A61K 33/38* | (2006.01) | |
| *A61K 47/48* | (2006.01) | |
| *A61K 47/32* | (2006.01) | |
| *A61L 15/16* | (2006.01) | |
| *A61L 15/46* | (2006.01) | |
| *A61L 15/00* | (2006.01) | |
| *A61K 47/00* | (2006.01) | |

(52) U.S. Cl.
CPC ............. *A61L 15/46* (2013.01); *A01N 59/16* (2013.01); *A61K 33/38* (2013.01); *A61K 47/48984* (2013.01); *A61L 2300/104* (2013.01); *A61L 2300/106* (2013.01); *A61L 2300/404* (2013.01); *A61L 2300/602* (2013.01)
USPC ........... 424/405; 424/445; 424/447; 424/618; 424/661; 514/772.1; 514/772.5; 514/772.6

(58) Field of Classification Search
CPC ....... A01N 59/16; A01N 25/10; A01N 59/00; A01N 2300/00; A61K 33/38; A61K 47/48984; A61K 47/32; A61L 15/46; A61L 15/16; A61L 15/00; A61L 2300/104; A61L 2300/106; A61L 2300/404; A61L 2300/602
USPC ................. 424/405, 445, 447, 618, 661; 514/772.1, 772.5, 772.6
See application file for complete search history.

(56) References Cited

U.S. PATENT DOCUMENTS

| | | | |
|---|---|---|---|
| 3,650,818 A | 3/1972 | Marzocchi et al. | |
| 4,859,719 A | 8/1989 | Ofstead | 523/108 |
| 4,919,662 A | 4/1990 | Knoll et al. | 623/6 |
| 5,019,096 A | 5/1991 | Fox et al. | 600/36 |
| 5,326,567 A | 7/1994 | Capelli | 424/405 |
| 5,360,609 A | 11/1994 | Wellinghoff | 514/772.3 |
| 5,631,300 A | 5/1997 | Wellinghoff | 514/772.3 |
| 5,639,295 A | 6/1997 | Wellinghoff et al. | 106/15.05 |
| 5,650,446 A | 7/1997 | Wellinghoff et al. | 514/772.3 |
| 5,662,913 A | 9/1997 | Capelli | 424/405 |
| 5,668,185 A | 9/1997 | Wellinghoff | 514/772.3 |
| 5,695,814 A | 12/1997 | Wellinghoff et al. | 427/213 |
| 5,705,092 A | 1/1998 | Wellinghoff et al. | 252/187.21 |
| 5,707,739 A | 1/1998 | Wellinghoff et al. | 428/403 |
| 5,709,870 A | 1/1998 | Yoshimura et al. | 424/404 |
| 5,744,151 A | 4/1998 | Capelli | 424/405 |
| 5,863,548 A | 1/1999 | Elder | 424/408 |
| 5,888,528 A | 3/1999 | Wellinghoff et al. | 424/405 |
| 5,914,120 A | 6/1999 | Wellinghoff et al. | 424/406 |
| 5,922,776 A | 7/1999 | Wellinghoff et al. | 514/772.3 |
| 6,046,243 A | 4/2000 | Wellinghoff et al. | 514/772.3 |
| 6,277,408 B1 | 8/2001 | Wellinghoff et al. | 476/53 |
| 6,605,304 B1 | 8/2003 | Wellinghoff et al. | 424/489 |
| 6,605,751 B1 | 8/2003 | Gibbins et al. | 602/41 |
| 6,669,981 B2 | 12/2003 | Parsons et al. | 427/2.31 |
| 6,716,895 B1 | 4/2004 | Terry | 523/122 |

FOREIGN PATENT DOCUMENTS

| | | |
|---|---|---|
| GB | 2392913 | 3/2004 |
| WO | 2000/12100 A1 | 3/2000 |
| WO | WO 00/69775 | 11/2000 |
| WO | 2001/43788 A2 | 6/2001 |

OTHER PUBLICATIONS

U.S. Appl. No. 11/215,739, filed Aug. 30, 2005, Wellinghoff.
Abuskhuana et al., "Synthesis, structure and anti-fungal activity of dimeric Ag(I) complexes containing bis-imidazole ligands," *Polyhedron*, 23:1249, 2004.
Avent et al., "The dissolution of silver-sodium-calcium-phosphate glasses for the control of urinary tract infections," *J. Non-Crystalline Solids*, 328:31, 2003.
Belloni, "Photography: enhancing sensitivity by silver-halide crystal doping," *Rad. Phys. Chem.*, 67:291, 2003.
Bowler et al., "Microbbicidal properties of a silver-containing hydrofiber dressing against a variety of burn wound pathogens," *J. Burn Care and Rehab.*, 25(2):192, 2004.

(Continued)

*Primary Examiner* — John Pak
*Assistant Examiner* — Nathan W Schlientz
(74) *Attorney, Agent, or Firm* — Grossman, Tucker et al

(57) ABSTRACT

Disclosed are compositions comprising a hydrophilic polymer, a hydrophobic polymer, a silver ion, and a chlorite anion, wherein the silver ion associates with at least one hydrophilic or hydrophobic polymer, and wherein the chlorite ion associates with the hydrophilic polymer. Also disclosed are methods of making a photo-stable silver ion and chlorite ion containing wound dressing and methods of reducing or preventing infection of a wound by using the compositions and wound dressings of the present invention.

27 Claims, No Drawings

(56) References Cited

OTHER PUBLICATIONS

Dowsett, "An overview of acticoat dressing in wound management," *Br. J. Nursing*, 12(19):S44-S50, 2003.

Engelmeyer et al., "A novel bioreactor for the dynamic flexural stimulation of tissue engineered heart valve biomaterials," *Biomaterials*, 24, 2523, 2003.

Galeano et al., "Inactivation of vegetative cells, but not spores, of *Bacillus anthracis*, *B. cereus*, and *B. subtilis* on stainless steel surfaces coated with an antimicrobial silver- and zinc-containing zeolite formulation," *Appl. Environ. Microbiol.*, 69(7):4329, 2003.

Han et al., "Decontamination of *Bacillus thuringienisis* spores on selected surfaces by chlorine dioxide gas," *J. Environmental Health*, 66(4): 16, 2003.

Henglein, "Physicochemical properties of small metal particles in solution: 'microelectrode' reactions, chemisorption, composite metal particles, and the atom-to-metal transition," *J. Phys. Chem.*, 97:5457, 1993.

Holder et al., "Assessment of a silver-coated barrier dressing for potential use with skin grafts on excised burns," *Burns*, 29:445, 2003.

Iwasaki et al., "Platelet compatible blood filtration fabrics using a phosphorylcholine polymer having high surface mobility," *Biomaterials*, 24, 3599, 2003.

Jones et al., "Controlling wound bioburden with a novel silver-containing hydrofiber dressing," *Wound Repair Regen.*, 12(3):288, 2004.

Jose et al., "Effect of phthalates on the stability and performance of $AgBF_4$-PVP membranes for olefin/paraffin separation," *Chem. Commun.*, 2046, 2001.

Kang et al., "Highly stabilized silver polymer electrolytes and their application to facilitated olefin transport membranes," *J. Membrane Sci.*, 236:163, 2004.

Kim et al., "Silver polymer electrolytes by π-complexation of silver ions with polymer containing c=c bond and their application to facilitated olefin transport membranes," *J. Membrane Sci.*, 237:199, 2004.

Kim et al., "π-Complexes of polystyrene with silver salts and their use as facilitated olefin transport membranes," *J. Poly. Sci., Part B: Poly. Phys.*, 42:2263, 2004.

Kim et al., "Structural changes silver polymer electrolytes: comparison between poly(2-ethyl-2-oxazoline) and poly(n-vinyl pyrrolidone) complexes with silver salt," *J. Poly. Sci.: Part B: Poly. Phys.*, 42:232, 2004.

Kim et al., "Formation of silver nanoparticles induced by poly(2,6-dimethyl-1, 4-phenylene oxide," *Langmuir*, 17:5817, 2001.

Lee et al., "Zwitterionic silver complexes as carriers for facilitated-transport composite membranes," *Angew. Chem. Int. Ed.*, 43:3053, 2004.

Lee et al., "Self-Assembly of biocidal nanotubes from a single-chain diacetylene amine salt," *J Am Chem Soc*, 283:295, 2004.

Lee et al., "Hydrogen bonding in polymer blends. 4. blends involving polymers containing methacrylic acid and vinylpyridine groups," *Macromol.*, 21:954, 1988.

Mostafavi et al., "Ultra-slow aggregation process for silver clusters of a few atoms in solution," *Chem. Phys. Lett.*, 167(3):193, 1990.

Mostafavi et al., "Complexation of silver clusters of a few atoms by a polyanion in aqueous solution: pH effect correlated to structural changes," *Chem. Phys. Lett.*, 169(1-2):81, 1990.

Mostafavi et al., "STM identification of silver oligomer clusters prepared by radiolysis in aqueous solution," *Chem. Phys. Lett.*, 218(1-2):115, 1994.

Mussini et al., "Surface screening effects by specifically absorbed halide anions in the electrocatalytic reduction of a model organic halide at mono- and polycrystalline silver in acetonitrile," *J. Electroanalytical Chem.*, 552:213, 2003.

Ng, "Ionomeric blends of poly(ethyl acrylate-*co*-4-vinylpyridine) with zinc-neutralized sulfonated poly(ethylene terephthalate). 1. effect of specific interactions upon the amorphous phase," *Macromol.*, 27:3027-3032, 1994.

Pappenfus et al., "Ionic conductivity of a poly(vinylpyridinium)/silver iodide solid polymer electrolyte system," *Solid State Ionics*, 171:41, 2004.

Park et al, "Preparation and characterization of activated carbon fibers supported with silver metal for antibacterial behavior, "*J Membrane Sci.*, 17:285, 2003.

Rodriguez et al., "Thermal behavior and electrical conductivity of poly(vinyl pyridine)/copper complexes," *Adv. Polym. Tech.*, 19(2):113, 2000.

Ruokolainen, "Poly(4-vinyl pyridine)/zinc dodecyl benzene sulfonate mesomorphic state due to coordination complexation," *Macromol.*, 28:7779, 1995.

Shin et al., "Self-assembly between silver(1) and di- and tri-2-pyridines with flexible spacer," *Inorg. Chem.*, 42:2977, 2003.

Solymosi, "The thermal stability and some physical properties of silver chlorite, chlorate and perchlorate," Zeitshrift fur Physikalische Chemie-Frankfurt, 57(1-2) S: 1, 1968.

Troupis et al., "Photocatalytic reduction—recovery of silver using polyoxometalates," *Appl. Catalysis B: Environ.*, 42:305, 2003.

Wellinghoff et al., "Structure-property relationships in poly (n-vinyl pyrrolidone)-phenoxy-water gels," *J. Poly. Sci., Part B: Poly. Phys.*, 29(2):247, 1991.

Xu et al., "Compatibilization of blends of polystyrene and zinc salt of sulfonated polystyrene by poly(styrene-*b*-4-vinylpyridine) diblock copolymer," *Polymer*, 40:2239, 1999.

Yi et al., "Preparation of new crosslinked chitosan with crown ehter and their absorption for silver ion for antibacterial activities," *Carbohydrate Polymers*, 53:425, 2003.

Young et al., "Mechanisms of killing of *Bacillus subtilis* spores by hypochlorite and chlorine dioxide," *J. Appl. Microbiology*, 95: 54, 2003.

Zheng and Mi, "Miscibility and intermolecular specific interactions in blends of poly(hydroxyether of bisphenol a) and poly (4-vinyl pyridine)," *Polymer*, 44:,1067, 2003.

Office Action mail dated Jun. 11, 2009 issued in U.S. Appl. No. 11/215,739.

Malynych et al., Poly(Vinyl Pyridine) as a Universal Surface Modifier for Immobilization of Nanoparticles, J. Phys. Chem. B, 2002, pp. 1280-1285, vol. 106, No. 6.

U.S. Office Action dated Apr. 28, 2010 issued in U.S. Appl. No. 11/215,739, 19 pages.

U.S. Office Action dated Jun. 21, 2011 issued in related U.S. Appl. No. 11/215,739, 20 pages.

U.S. Office Action dated Sep. 13, 2012 issued in related U.S. Appl. No. 11/215,739, 17 pages.

Acrylate Polymer obtained online via Wikipedia on Sep. 8, 2012 by (http://en.wikipedia.org/wiki/Acrylate_polymer).

Acrylic Acid obtained online via Wikipedia on Sep. 10, 2012 by (http://en.wikipedia.org/wiki/Acrylate_acid).

2-Propenoic Acid, polymer with 1,3-butadiene and ethenylbenzene obtained online Sep. 7, 2012 by (http://www.guidechem.com/reference/dic-450103.html).

U.S. Office Action dated Dec. 3, 2013 issued in related U.S. Appl. No. 11/215,739, 16 pages.

BIOCIDAL FIBROUS AND FILM MATERIALS COMPRISING SILVER AND CHLORITE IONS

RELATED APPLICATION(S)

This application claims the benefit of U.S. Provisional Application No. 60/605,569, filed Aug. 30, 2004, the contents of which are incorporated by reference.

BACKGROUND OF THE INVENTION

1. Field of the Invention

The present invention relates to antimicrobial materials and methods of preparing the same for delivering biocidal agents to wounds. More specifically, the invention relates to hydrophilic/hydrophobic polymer blends that can be used to control the rate of release of silver ions and chlorite ions to a target site such as a wound.

2. Background of the Invention

Skin wounds (e.g., cuts, scraps, lesions, lacerations, burns etc.) often become infected. This can slow or complicate the healing process, and in some instances, prevent healing from occurring. Infection can also increase the costs associated with treating the wound.

Wound dressings have been used to protect the wound from external environments and to reduce the possibility of wound infection. The use of topical antimicrobial agents can be used in conjunction with wound dressings. Antimicrobial agents have also been used in wound dressings.

Chlorine dioxide is a known biocidal agent that can penetrate through both inorganic and organic amorphous material and is effective in killing mold and bacterial spores, viruses and vegetative bacteria. As an oxidizing gas it can penetrate orifices and have biocidal action against difficult to kill bacterial spores even on dry porous substrates (Han et al., 2003). The mechanism of killing by chlorine dioxide has been investigated (Young et al., 2003).

Silver ion is another biocidal agent that can be incorporated in polymer films and fibers. A problem associated with the use of silver ions is that they are sensitive to light which causes discoloration of the silver ion containing material—an aesthetically un-pleasing event. Attempts have been made at creating photo and thermally stabilized silver ion formulations for wound dressing.

U.S. Pat. Nos. 5,326,567, 5,662,913, and 5,744,151 describe stabilizing silver ion in a oligoethylene oxide complex in an environment containing an excess of halide ions. A problem with this technique is that it appears to be suitable for use in solutions only and are sensitive to solvent and salt conditions.

Wound dressings containing silver nanoparticles are highly colored due to the plasmon resonance of the silver particles or have a metallic sheen, especially if the polymer films or fibers are overcoated with continuous metal (Dowsett, 2003; Holder et al., 2003). Silver nanoparticles have been microencapsulated in methyl methacrylate polymer and have shown biocidal activity (Lee et al., 2004).

Light stable compositions with allantoin (U.S. Pat. No. 5,863,548) and carboxymethylcellulose (U.S. Pat. No. 5,709,870) have also been attempted. The use of anionic polysaccharides to stabilize the silver ion are explained in U.S. Pat. Nos. 6,605,751 and 6,669,981. Other controlled release, silver ion based products, are ammonium complexed silver ion (Contree™ by Coloplast) and silver calcium phosphate Arglaes™ (Medline) (Avent et al., 2003) and silver ion infiltrated zeolites (AgION). Crown ethers that selectively bind silver ion have been copolymerized with chitosan (Yi et al., 2003).

SUMMARY OF THE INVENTION

The present invention overcomes deficiencies in the art by providing compositions and methods for their use that can be used in biocidal applications, such as wound dressings. One aspect of the present invention includes a composition that comprises a hydrophilic polymer comprising a chlorite anion, a hydrophobic polymer, and a silver ion, wherein the silver ion associates with at least one hydrophilic or hydrophobic polymer. The silver ion can associate with at least one hydrophilic polymer and at least one hydrophobic polymer. The silver can bridge at least one hydrophilic polymer with at least one hydrophobic polymer in certain embodiments. The association between the silver ion and the hydrophilic polymer or the hydrophobic polymer can be characterized as an ionic bond, a covalent bond, a co-ordinate bond, or an electrostatic interaction. The silver ion can be obtained from $AgBF_4$, $AgPF_6$, $AgSO_3CF_3$, $AgClO_4$, $AgNO_3$, n-alkylArSO$_2$Ag, or n-alkylCOOAg.

The chlorite anion can be associated with the hydrophilic polymer by an electrostatic interaction. In other aspects, the chlorite anion can be associated with a cation. Non-limiting examples of cations include $Na^+$, $K^+$, $Li^+$, $Cs^+$ $Rb^+$, or a tetra-alkylammonium cation, and mixtures thereof.

The hydrophobic or hydrophilic polymer can also include an anionic group. The silver ion can associate with the anionic group. An example of an anionic group is a —$COO^-$ group. In other embodiments, the hydrophilic or hydrophobic polymers can be substituted with a quaternary nitrogen azaaromatic or aliphatic group, wherein the quaternary nitrogen in the azaaromatic or aliphatic group comprises an anion. The anion can be a $Cl^-$ anion.

The compositions of the present invention can include about 0.01%, 0.02%, 0.03%, 0.04%, 0.5%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 40%, 50%, or more by weight of silver ion. In certain embodiments, the composition include about 1% to about 10% by weight of silver ion. The compositions can also include about 0.01%, 0.02%, 0.03%, 0.04%, 0.5%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 40%, 50%, or more by weight of chlorite ion. In certain aspects, the composition include about 1% to about 10% by weight of chlorite ion. The compositions can also include about 10%, 15%, 20%, 25%, 30%, 35%, 40%, 50%, 60%, 70%, 80%, 90%, 95%, or 99% by weight of a hydrophilic polymer. In certain embodiments, the composition includes about 20% to about 80% by weight of hydrophilic polymer. In other aspects, the compositions can include about 10%, 15%, 20%, 25%, 30%, 35%, 40%, 50%, 60%, 70%, 80%, 90%, 95%, or 99% by weight of a hydrophobic polymer. In certain aspects, the composition include about 20% to about 80% by weight of hydrophobic polymer. In other non-limiting embodiments, the hydrophilic/hydrophobic polymer ratio can be about 1/10, 1/9, 1/8, 1/7, 1/6, 1/5, 1/4, 1/3, 1/2, 1/1, 2/1, 3/1, 4/1, 5/1, 6/1, 7/1, 8/1, 9/1, or 10/1. In certain aspects, the ratio is between about 1/4 to about 4/1.

In other aspects, the composition can be transparent. The composition can also be formulated to be a controlled release composition, wherein the release of silver ion or chlorite ion is to be controlled. The controlled release of silver or chlorite ion can be varied by changing the hydrophilic/hydrophobic polymer ratio. In certain instances, the composition is comprised on the surface of a medical device. Non-limiting examples of medical devices include a scalpel, a tong, a retractor, a scalpel, or a glove. The compositions of the present invention can be comprised in a wound dressing. The compositions can be the wound dressing. The silver ion or chlorite ion can be photo-stable or thermally-stable.

Non-limiting examples of hydrophobic polymers that can be used with the present compositions include poly(hydroxyether of bisphenol A), ethylene, styrene, alkyl acrylates, saccharide acetates, copolymers of disulfonyl chloride, diphenyl ether and biphenyl, copolymers of bisphenol A and dichlorodiphenylsulfone, aromatic polyimides, aromatic polyesters, cellulose acetate polymers, polycarbonate polymers, polyvinylidene fluoride, copolymers of hexafluoropropene and vinylidene fluoride, polymethylmethacrylate, polybenzylmethacrylate, polyphenylmethacrylate, polyvinyl cinnamate, polyvinylbutyral, or polyphenylene ether sulfone. The hydrophobic polymers can include a partially neutralized carboxylic acid group from acrylic acid monomer, a methacrylic acid monomer, a maleic acid or hydrolyzed anhydride monomer, or a substituted phthalic acid or hydrolyzed acid anhydride monomer or a hydrolyzed α-hydroxyacid ester, wherein the anionic form complexes the silver ion and wherein the acid form generates chlorine dioxide from chlorite anion. Non-limiting examples of hydrophilic polymers that can be used with the present compositions include a vinyl pyridine polymer, a vinyl imidazole polymer, N-vinylpyrrolidone (PVNP), N,N-dimethylacrylamide, vinyl methyl ether, N-vinylacetamide, or ethyl oxazoline (PEOX).

In certain instances, the silver ion can associate with a hydrophilic polymer. The silver ion, for example, can associate with a pyridine group of a polyvinylpyridine hydrophilic polymer through a metal co-ordination bond. In other aspects, the silver ion can associate with a hydrophobic polymer. The silver ion, for example, can bond to an arene group of a styrene-acrylic acid copolymer through a d-π interaction.

In another embodiment of the present invention, there is provided a method of making a photo-stable silver ion containing wound dressing comprising (a) obtaining a composition comprising: (i) a hydrophilic polymer comprising a chlorite anion; (ii) a hydrophobic polymer; and (iii) a silver ion, wherein the silver ion associates with at least one hydrophilic or hydrophobic polymer, wherein the composition reduces or prevents discoloration of the wound dressing, and (b) incorporating the composition of step (a) into a wound dressing.

There is also provided a method of reducing or preventing infection of a wound comprising: (a) obtaining a wound dressing comprising: (i) a hydrophilic polymer comprising a chlorite anion; (ii) a hydrophobic polymer; and (iii) a silver ion, wherein the silver ion associates with at least one hydrophilic or hydrophobic polymer, and (b) applying the wound dressing to the wound. Non-limiting examples of infections include bacterial, viral, or fungal infections.

In another aspect of the present invention, there is provided a method of making a biocidal material comprising: (1) obtaining a solution of an organosoluble silver salt in an organic solution of a sodium, potassium, lithium or quaternary ammonium or phosphorous cation salt of a carboxylate and/or sulfonate substituted hydrophobic polymer; (2) washing the organic layer with a water solution of a silver salt with or without the aid of a phase transfer agent to concentrate the alkali or quaternary cation in the water phase; (3) washing the organic phase with neat water; (4) dissolving an organosoluble hydrophilic polymer containing chlorite anion in the organic phase to make a mobile solution; and (5) spraying or casting the mobile solution onto or infused into substrates to produce coated objects by solvent evaporation.

It is contemplated that any embodiment discussed in this specification can be implemented with respect to any method or composition of the invention, and vice versa. Furthermore, compositions and kits of the invention can be used to achieve methods of the invention.

"Silver" includes all silver salts or silver compounds, including, but not limited to, silver chloride, silver phosphate, silver sulfate, silver iodide, or silver bromide. The active form of the silver salt is the silver ion.

The terms "inhibiting," "reducing" or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Infection can affect the healing process of wounds, and in some cases, inhibited the healing process altogether. The present invention provides compositions that include both hydrophilic and hydrophobic polymers. The compositions can be placed on, integrated into, or processed as wound dressings. The delivery of biocidal agents such as silver and chlorite ions (chlorine dioxide) can be performed in a controlled manner. The silver ions and chlorite ions can also be photo-stable and/or thermally stable. These and other aspects of the present invention are described in further detail.

1. Silver Ions ($Ag^+$)

Silver ions exhibit biocidal properties by reacting with the surfaces of bacteria and extracellular viruses, preventing them from obtaining the energy necessary to survive. Mammalian cells are not affected by silver. Because silver ions are sensitive to light, methods of stabilizing silver are important.

The stabilization of silver ion relative to the growth of large silver metal clusters in the presence of a reducing agent is known to depend on the size of the silver atom cluster containing the positive charge (Belloni, 2003). The redox potential, $E^O_{NHE}$ ($Ag^+_n/Ag_n$), and thus the ease of conversion of silver ion to a single silver atom, increases from −1.6V for n=1, to 0V for n=10, to +0.799 V for n=600. The strategy in photostabilization of silver ion is to prevent the growth of $Ag^+_n$ to a critical size. This can be accomplished by loading an excess amount of halogen ions, which absorb silver ion, into a hydrogel (U.S. Pat. Nos. 6,605,751 and 6,669,981). Halogen ions stabilize silver ion and silver ion cluster from further reduction. Iodide and bromide have been shown to be more effective than chloride in stabilizing the ion-metal cluster in a hydrogel against (Mussini et al., 2003). This is illustrated in table 1 below:

TABLE 1

| Complex | $E^0_{NHE}$ ($Ag^+_{oo}/Ag^{H2O}_{oo}$) | $E^0_{NHE}$ ($Ag^+_n/Ag^{H2O}_n$) | $E^0_{NHE}$ ($Ag^+_{oo}/Ag^{MeCN}_{oo}$) |
|---|---|---|---|
| $NH_3$ | −2.200 | | |
| $S^{-2}$ | −0.705 | | |
| $I^-$ | −0.152 | | −1.24 |
| $CN^-$ | −0.020 | −0.400 (n = 7), −2.4 (n = 1) | |
| $S_2O_3^{-2}$ | +0.010 | | |
| $Br^-$ | +0.071 | | −1.12 |
| $SCN^-$ | +0.090 | | |
| $Cl^-$ | +0.222 | | −1.01 |
| $Ac^-$ | +0.640 | | |
| $SO_4^{-2}$ | +0.650 | −0.400 (n = 5) | |
| — | +0.799 | −1.700 (n = 2) | |

This is also in agreement with the use of polyoxometalates whose photogenerated electrons will reduce uncomplexed silver ion but not in the presence of high concentrations of thiosulfate, $S_2O_3^{-2}$. In this case the hole of the electron hole pair is reduced by $(CH_3)_2COH$ to the radical ion and then to acetone (Troupis et al., 2003). This is illustrated in table 2 below.

TABLE 2

| | $E^0_{redox}$ |
|---|---|
| $SiW_{12}O_{40}^{-4/-5}$ | +0.057 |
| $PW_{12}O_{40}^{-3/-4}$ | +0.221 |
| $P_2Mo_{18}O_{62}^{-6/-8}$ | +0.664 |

If reduction of monomeric silver ion does occur, growth of the silver clusters can be terminated at an early stage [e.g., $(Ag_4Ag_n)^{+n}$ and especially $Ag_4^{+2}$ (oxygen stable) (Henglein, 1993) by complexation with a polyacrylate polymer (Mostafavi et al., 1994; Mostafavi et al., 1994; Mostafavi et al., 1990a; 1990b). The protonated form of the polymer is less efficient in preventing growth. Stronger nucleophiles than carboxylate will displace the cluster from the polymer and permit growth. A photostable form of silver ion or small silver ion-metal clusters would be achieved by complexation of the silver ion a polymeric complexing agent that also compensates the positive charge.

Bridged pyridine compounds (Shin et al., 2003) and polyvinylpyridine (PVP) (Pappenftis et al., 2004) can form air and photostable complexes with $Ag^+$ and $Cu^+$ salts (Rodriguez et al., 2000). Bridged imidazole compounds can complex with $Ag^+$ to yield fungicides (Abuskhuana et al., 2004).

Silver ion containing polymers also have utility in selective separation membranes for hydrocarbons since $Ag^+$ selectively binds with alkenes and aromatics through a d-π complex and with amides, esters, and ethers through Lewis acid-base interactions. Very high concentrations of low lattice energy silver salts such as $AgBF_4$, $AgPF_6$, $AgSO_3CF_3$, or $AgClO_4$ can be dissolved in poly(n-vinylpyrrolidone) (PNVP) and poly (2-ethyl-2-oxazoline) (PEOX) by casting a THF solution (Kim et al., 2004a). These films are susceptible to photoreduction to silver nanoparticles aided by the complexing heteroatom. Poly (2,6 dimethyl-1,4-phenylene oxide) forms complexes with low lattice energy silver salts but the diaryl ether bond is susceptible to cleavage by the complexed $Ag^+$ ion (Kim et al., 2001).

Increased stability in PNVP has been obtained by complexing the silver ion with a combination of heteroatom and aromatic chelation using a phthalate ester monomer (Jose et al., 2001) and in neat poly (ethylene phthalate) (Kang et al., 2004). Nonionic carbohydrate surfactants such as n-octyl β-D-glucopyranoside (Park et al., 2003) function by stabilizing the surface of silver metal clusters and by a $Ag^+$ chelation by adjacent hydroxyl groups. Zwitterionic silver complexes between Ag salts and imidazolium N-alkyl sulfonates are also photostable (Lee et al., 2004).

Silver salts can be dissolved in high mole fractions in completely apolar, hydrophobic polymers containing no heteroatoms, such as polystyrene (Kim et al., 2004b) and poly (hexamethylene vinylene) (Kim et al., 2004c). In addition the photo and thermal stability of d-π complexed $Ag^+$ with regard to formation of silver particles is improved because of the absence of susceptible heteroatoms such as ether and amide groups.

2. Chlorine Dioxide Generated from Chlorite Anions

Chlorite ion, $ClO_2^-$, and chlorine dioxide, $ClO_2$, exhibit biocidal properties. Chlorine dioxide, the more powerful biocide of the two, can be used as an antimicrobial agent at a concentration as low as 0.1 ppm and over a wide pH range. Chlorine dioxide gas readily dissolves in water and organic materials such as lipids and thus can penetrate cell walls and cell membranes and react with vital amino acids and proteins in the cytoplasm and cell wall and membrane to exert biocidal action.

A chlorite ion, from which chlorine dioxide is generated through acidification or through photo generation using a catalyst, can be obtained from any type of chlorite salt. Non-limiting examples include alkali metal chlorites, alkaline earth metal chlorites, and any other transition metals, inner transition metal chlorites and/or polymeric salts. Examples of metal chlorites include calcium chlorite, barium chlorite, magnesium chlorite, lithium chlorite, sodium chlorite, and potassium chlorite.

3. Biocidal Fabrics and Films

The biocidal fabrics and films of the present invention include hydrophobic and hydrophilic polymers that comprise $Ag^+$ and chlorite ions that can be used for controlled release of the $Ag^+$ and chlorine dioxide to a target site such as a wound. The polymer blend compositions also photo and thermally stabilize these ions. The compositions of the present invention can be used, for example, to (1) kill mold and bacterial spores and vegetative bacteria and viruses (2) reduce or prevent discoloration of the wound dressing. A biocidal device can be created where chlorine dioxide can be first released to rapidly kill spores which are not affected by $Ag^+$ alone. Subsequently, a sustained release of $Ag^+$ to sustain wound sterility over longer periods can occur. Because both chlorite anion and chlorine dioxide are strong oxidants, reduction of silver ion to non-biocidal and non-esthetic silver metal is prevented.

The compatible blend of hydrophilic and hydrophobic polymers can swell with water exposure to form flexible and strong hydrogels. The rate of release of $Ag^+$ and chlorine dioxide from chlorite anions, can be controlled or adjusted by varying the hydrophobic/hydrophilic polymer ratio. The equilibrium water content of the gel increases by increasing the ratio of the hydrophilic polymer to hydrophobic polymer (Wellinghoff et al., 1991; U.S. Pat. No. 4,919,662; U.S. Pat. No. 4,859,719). Small angle X-ray and thermal analysis (DSC) experiments reveal that the interfacial adhesion in the hydrogel comprising hydrophilic and hydrophobic phases is maintained by the bridging PNVP component which is soluble in both phases.

a. Hydrophobic Polymers

Non-limiting examples of hydrophobic polymers that can be use with the present invention include poly(hydroxyether of bisphenol A) (phenoxy polymer), ethylene, styrene, alkyl acrylates, saccharide acetates, copolymers of disulfonyl chloride, diphenyl ether and biphenyl, copolymers of bisphenol A and dichlorodiphenylsulfone, aromatic polyimides, aromatic polyesters, cellulose acetate polymers, polycarbonate polymers, polyvinylidene fluoride, copolymers of hexafluoropropene and vinylidene fluoride, polymethylmethacrylate, polybenzylmethacrylate, polyphenylmethacrylate, polyvinyl cinnamate, polyvinylbutyral, or polyphenylene ether sulfone. Copolymers of vinyl chloride and vinyl acetate can also be copolymerized with comonomers containing sulfonic acid or carboxylic acid groups such as acrylic or methacrylic acid, maleic or phthalicacid, carboxymethylsaccharide comonomers, styrene sulfonate. The hydrophobic polymers and copolymers can be mixed with small amounts of alkyl alcohol containing co-monomers (e.g., vinyl alcohol) to provide sites for compatibilization with hydrophilic polymers.

Because chlorite anion is unstable in acidic solution, carboxylate silver-alkali metal-quaternary ammonium salts of the hydrophobic polymer can be mixed with the chlorite. A $pH>8$ can be maintained in the presence of water.

b. Hydrophilic Polymers

Hydrophilic copolymers can be based upon vinyl pyridine or vinyl imidazole, with or without comonomers containing vinyl alkyl amines. Hydrophilic polymer can also be selected from polymers prepared from N-vinylpyrrolidone (PVNP), N,N-dimethylacrylamide, vinyl methyl ether, N-vinylacetamide, ethyl oxazoline (PEOX), and the acylation of polyethyleneimine, all of which will be stable in the presence of chlorine dioxide. Silver ion will not be as stable in blends containing amide groups due to the possible photoreaction with the amide moiety unless it is substantially stabilized by a chelating carboxylate (phthalates, etc.).

c. Hydrophobic and Hydrophilic Blends

Poly (4 (or 2)-vinylpyridine) is a strong $Ag^+$ chelator and will also form compatible blends with many hydrophobic polymers such as phenoxy polymer (Zheng and Mi, 2003) and poly (ethylene-co-methacrylic acid) (Lee et al., 1988). Ionomeric blends will also form between poly (ethyl acrylate-co-4-vinyl pyridine) and zinc neutralized sulfonated poly (ethylene terephthalate) (Ng, 1994). With an increased zinc content, $Zn^{+2}$ will complex with both the pyridine and sulfonate side groups on adjacent polymer chains to produce compatible blends. Similar compatibility has been shown between the zinc salt of sulfonated polystyrene and poly (4-vinylpyridine) (Xu et al., 1999). The same mechanism drives the formation of mesomorphic blends between poly (4-vinylpyridine) and zinc dodecyl benzene sulfonate (Ruokolainen, 1995). In essence a compatible blend of a hydrophobic and hydrophilic polymer can be formed which can later be swollen to a uniform hydrogel if there are specific Lewis acid-base interactions between the polymer and/or intercomplexations through metal atoms. The films or fibers can subsequently be swollen to a hydrogel in the presence of water.

Hydrophilic polymers of the present invention can also be blended with hydrophobic polymers known to those of ordinary skill in the art, including the hydrophobic polymers disclosed in this specification.

An alternative source of acid groups that are especially useful for chlorine dioxide release through acidification of blends containing chlorite anion is through the in situ hydrolysis of hydrophobic monomers with the comonomers containing the esters of α-hydroxy acids such as lactic and glycolic acid (Wellinghoff et al., 1991; U.S. Pat. No. 5,922,776) which are known for their biocompatility and safety.

In one embodiment, the hydrophilic and hydrophobic polymers can be co-cast into compatible blend films with various silver salts ($AgBF_4$, $AgPF_6$, $AgSO_3CF_3$, $AgClO_4$, $AgNO_3$ etc) and/or chlorite ions. The silver salt can also be complexed as n-alkylArSO$_2$Ag or n-alkylCOOAg to produce a mesomorphic blend with the hydrophilic polymer through interaction of the partially filled co-ordination sphere of $Ag^+$ carboxylate or sulfonate salt with the azaaromatic groups.

d. Silver Doped Polymers

The silver ion may be precomplexed by partial ion exchange of a silver salt with the alkali metal carboxylic acid salt of the carboxylic acid comonomer substituted hydrophobic polymer in a common solvent such as tetrahydrofuran or methylene chloride prior to mixing and processing with the sodium chlorite hydrophilic polymer. For example, the organic soluble components, silver salt and partial sodium salt of the carboxylate substituted hydrophobic polymer, may be mixed in an organic solvent such as methylene chloride and the water soluble product, $NaO_2SCF_3$, selectively extracted by a saturated aqueous solution of a silver salt. Alternatively, a phase transfer catalyst and base may be added to the saturated aqueous silver salt solution and silver introduced by phase transfer into an organic phase containing the carboxylate or sulfonate substituted hydrophobic polymer.

Because excess halogen anion is known to photostabilize silver complexes by decreasing the redox potential of $Ag^+$ and $Ag^+_n$ through specific surface adsorption, the hydrophilic polymer may also contain the halogen anion salts of quaternary nitrogen substituted monomers such as N-alkyl vinyl pyridines or imidazoles, which can be prepared by partially N-alkylating the poly azaaromatic, or vinyl alkyl quaternary amines. These quaternary groups are known to exhibit biocidal action in their own right.

One can also stabilize silver ions by using an organic or organic-aqueous solution of a silver salt to deliver silver into a fabric or film consisting of a hydrophilic, carboxylate substituted polysaccharide. Stabilizing agents such as chloride or ammonium compounds are then added to decrease the redox potential of the absorbed $Ag^+$. Upon ion exchange the sodium or other alkali cation will remain as a precipitated salt in the polymer matrix. In addition, the silver loading into the interior of the polymer is limited by diffusion, especially in the case of thicker fibers and films.

U.S. Pat. No. 6,605,751 explains that the surface regions of the hydrogel polymer can be first exposed to a non-swelling water-alcohol solution chloride solution. AgCl nanocrystals are then precipitated onto (into) the polymer with $Ag^+$ from an aqueous-alcohol solution. Because AgCl is photo-unstable and will rapidly convert to $Ag_n^+$ nanoclusters in the presence of reducing agents (proteins, wound exudates), $Cu^{+2}$ and $Fe^{+3}$ can be added into the mix to reoxidize any $Ag_n$ and prevent irreversible growth to nanoparticle size.

In another non-limiting embodiment of the present invention, the silver ion can associate with both hydrophilic and hydrophobic polymers. The silver ion, for example, can be used as a bridge between the hydrophilic and hydrophobic phases to improve compatibility. For example, the silver ion can associate with the pyridine group of a polyvinylpyridine hydrophilic polymer through a metal co-ordination bond. The silver ion can also associate with a negatively charged carboxylate group of a carboxylate substituted hydrophobic polymer, such as an acrylic acid-acrylic ester copolymer through an ionic interaction with some chelation. The silver ion can also bond directly to an arene group of a hydrophobic polymer such as a styrene-acrylic acid copolymer through a d-π interaction. In certain embodiments, the bridge should be strong enough to produce solubility and compatibilizaton of the hydrophilic and hydrophobic polymer and silver ion in a common solvent, but not so strong so as to produce a gel which cannot be processed. Once the blend is cast from solution, crosslinking can be used to achieve mechanical strength.

e. Chlorite and $Ag^+$ Doped Polymers

Chlorite anion is typically supplied in the form of sodium chlorite. The commercial product is a mixture of sodium chlorite, and sodium carbonate, which, because of the high basicity, is more stable than pure sodium chlorite. Neat sodium chlorite can be made by extracting the commercial material with methanol and crystallizing the pure sodium chlorite by concentrating the methanol solution.

Because sodium chlorite is soluble in lower alcohols, solutions of salt and silver complexing, hydrophilic polymers can be made in these solvents and mixed with organic solutions of a silver carboxylate substituted hydrophobic polymer. When the solutions are mixed, some of the silver is displaced from the carboxylate group to form insoluble silver chlorite nanoclusters which remain suspended in the polymer solution. The mole ratio of $ClO_2^-/Ag^+$ and complexing strength of the hydrophilic polymer can be used to control the percentage of chlorite associated with $Na^+$ or with $Ag^+$. In addition, hydrophilic, Lewis base comonomers such as vinyl pyridine or vinyl imidazole can serve to buffer any free acid groups present in the hydrophobic polymer preventing premature acidification and release of chlorine dioxide from the chlorite during polymer film processing. After hydration of the blend these groups can also perform a buffering action which lends itself to improved controlled release of chlorine dioxide.

Silver chlorite is a light yellow (absorption edge at 400 nm), partially covalently bound solid that precipitates from water when sodium chlorite is mixed with silver nitrate (Solymosi, 1968). The silver chlorite salt releases chlorine dioxide, chlorine and oxygen and decomposes explosively as a neat solid at 145° C. but will slowly disproportionate in the solid state at temperatures above 85° C. by the reaction:

$$3AgClO_2 \rightarrow 2AgClO_3 + AgCl$$

$AgClO_2$ is stable below this temperature in the absence of acid. Processing of the blends can therefore be performed in the vicinity of room temperature.

Upon acidification, the small amount of chlorite ion that is released from the silver salt into the water phase will decompose to chlorine dioxide. With less salt formation with silver ion more chlorite may be released increasing the generation rate of chlorine dioxide. Hydronium ion is released from pre-existing carboxylic acid groups substituted on one of the polymer components or those generated by anhydride or α-hydroxyester hydrolysis that occurs when the blend film hydrates:

$$5ClO_2^- + 4H^+ \rightarrow 4ClO_2 + 2H_2O + Cl^-$$

The redox potentials of chlorine dioxide and silver are listed below in table 3:

TABLE 3

| | $E^0_{redox}$ |
|---|---|
| $Ag^{+2}/Ag^+$ | +1.800 |
| $ClO_2/ClO_2^-$ | +0.950 (pH = 7) |
| $ClO_2^-/Cl^-$ | +0.370 (pH = 7) |
| $Ag_n^{+1}/Ag_n$ | −1.700 (n = 2) |

Both chlorite anion and chlorine dioxide will oxidize any silver metal that might form to silver ion. This can prevent the formation of silver clusters. This also minimizes coloring due to silver metal particles in the visible region of the spectrum, and maximizes the availability of silver ion, the biocidal form of silver. In addition, the chloride anion that is a byproduct of chlorine dioxide release will also serve to stabilize $Ag^+$. Finally, when silver chlorite clusters or nanoparticles form in the blend due to the association of chlorite anions from the hydrophilic phase and silver ions from the hydrophobic phase, the high insolubility of the salt in the absence of acid will limit the premature extraction and possible loss and dilution of chlorite into the aqueous phase during water swelling of the blend prior to generation of acid.

f. Construction and Operation of the Biocidal Fabrics and Films

A non-limiting embodiment of the present invention comprises partially cutting the polymer film/wound dressing into strips to obtain better wound contact and improved debridement upon removal. Alternatively, fibers may be solution extruded and spun into a non-woven fabric suitable as a biocidal wound covering. Electrospinning of the polymer composition is especially advantageous for making small pore wound dressings in situ and for making dressings with a strong capillary wicking action.

In another embodiment a solution of the silver-chlorite loaded blend system in an organic solvent is infused into an organic insoluble, non-woven or woven fiber network consisting of, for example, carboxymethyl cellulose and its derivatives, and then the solvent evaporated to coat the fiber scaffold. Depending on the rate of evaporation and the content of water in the organic solvent, some silver-sodium ion exchange may take place across the fiber scaffold-blend boundary. However, most of the silver reservoir is contained in the coating whose extent of swelling on the underlying fiber can be controlled by the hydrophilic/hydrophobic polymer ratio. A similar coating process has been used to make biocompatible, phosphorylcholine polymer modified, non-wovens made from poly (ethylene terephthalate) (Iwasaki et al., 2003) and poly 4-hydroxybutyrate coated poly(glycolide-lactide) based fabrics (Engelmeyer et al., 2003).

In certain instances, it may be advantageous to prepare the coating composition so that it swells with water to an extent greater than the underlying fiber. This can induce a compressive hoop stress at the fiber interface that would promote fiber-polymer blend adhesion.

4. Compositions of the Present Invention

A person of ordinary skill would recognize that the compositions of the present invention can include a varying range of $Ag^+$ concentrations, chlorite ion concentrations, hydrophilic polymer concentrations and hydrophobic polymer concentrations. In certain non-limiting embodiments, the compositions may comprise in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 99% or more by weight or volume of at least one $Ag^+$, chlorite ion, hydrophilic polymer, and/or hydrophobic polymer, and any range derivable therein. A person of ordinary skill in the art would understand that the concentrations or amounts of $Ag^+$, chlorite ions, hydrophilic polymers, and/or hydrophobic polymers can vary depending on the addition, substitution, and/or subtraction of additional materials.

The compositions of the present invention may also include additional antibacterial, antiviral, or antifungal agents, including but not limited to parabens (e.g., methylparabens, propylparabens), chlorobutanol, phenol, sorbic acid, thimerosal, or combinations thereof.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparing Biocidal Material

The biocidal material is made by first co-dissolving the silver salt with partially neutralized carboxylated hydrophobic polymer containing varying percentages of acid anhydride or α-hydroxy ester comonomer in a mobile organic solvent. The carboxylate counterianions may be $Na^+$, $K^+$, $Li^+$ or other monovalent cations such as tetraalkylammonium cations. Subsequently, the cation is extracted with a saturated aqueous solution of a silver salt. This allows for a more complete silver exchange. The contaminating alkali metal or tetraalkyl ammonium ion and its counterion are removed by phase transfer across the organic-water boundary. Removal of these byproducts yields a much more reliable product performance during processing by fiber spinning methods such as electrospinning. In addition, toxic counterions with certain formulation advantages may be employed since they are ultimately removed from the product. In the next step, the silver doped hydrophobic polymer is mixed with a lower alcohol solution of a sodium chlorite doped hydrophilic polymer to produce the final blend.

In another non-limiting embodiment, the biocidal material can be made by: (1) obtaining a solution of an organosoluble silver salt in an organic solution of a sodium, potassium, lithium or quaternary ammonium or phosphorous cation salt of a carboxylate and/or sulfonate substituted hydrophobic polymer; (2) washing the organic layer with a water solution of a silver salt with or without the aid of a phase transfer agent to concentrate the alkali or quaternary cation in the water phase; (3) washing the organic phase with neat water: (4) dissolving an organosoluble hydrophilic polymer in the organic phase to make a mobile solution; and (5) spraying or casting the mobile solution onto or infused into substrates to produce coated objects by solvent evaporation.

Example 2

Varying the Rates of $Ag^+$ and $ClO_2$ Controlled Release

Because the silver salt is complexed both in the hydrophobic and hydrophilic phases of the swollen blend, a mechanism exists for controlled release of silver ion over a wide range of rates by adjusting the relative silver ion binding potentials of the two phases through adjustments in the chemical structure of the constituent polymers.

In addition, the chlorine dioxide release rate may be independently controlled by changing the acid available as free carboxylic acid, and/or hydrolyzable acid anhydride and/or hydrolyzable α-hydroxyacid ester in the hydrophobic phase subsequent to blend hydration. A fast release of a large $ClO_2$ concentration, especially useful for biocidal action against spores, followed by a sustained slow release can be obtained by employing a large concentration of free carboxylic acid in the hydrophobic copolymer along with an acid generating acid anhydride and/or a-hydroxyacid ester comonomer which will supply acid at longer times after the initial hydration. The long term release can be further controlled by changing the ratio of glycolic acid/lactic acid ester comonomers. Hydrophobic blends containing a higher glycolic/lactic ratio will produce higher concentrations of chlorine dioxide sooner because of the more rapid hydrolysis to produce glycolic acid. This release may be tuned relative to the $Ag^+$ release to produce a wide range of biocidal products that act through direct contact (Ag$^+$) and gas diffusion over a considerable distance (ClO$_2$).

Example 3

Manufacture of Wound Dressings

The manufacture of wound dressings that can be used with the present invention are contemplated. A person of ordinary skill in the art would be able to make wound dressing with the knowledge available in the art. This can be done, for example, in the following manner:

A solution of the complexed silver and chlorite ions, hydrophobic and hydrophilic polymer in a low boiling organic solvent is first infiltrated into an insoluble carboxymethyl cellulose, non-woven wound dressing scaffold. The solvent is evaporated to produce a highly porous, coated product. Alternatively, a woven product may be infiltrated to produce a dressing with anisotropic mechanical properties.

In another variation, the same solution is cast from a biosafe solvent such as acetone directly onto the wound to produce a solid, flexible polymer film which will seal the wound and yet will be able to hydrate to permit fluid exchange and to cause controlled release of silver ion. The solution can be distributed via an applicator or by aerosol spray.

The polymer solution can also be used to directly produce a non-woven product by extrusion through an array of fine nozzles, subsequent evaporation of the low boiling solvent and fiber bonding in flight and then deposition on a substrate similar to the process known in the art to directly produce a fibrous non-woven product. Nanofibers may be produced by the process of electrospinning, also well known in the art.

Alternatively, the solution may be spun into continuous fibers and collected for later fabrication into a woven product or the polymer solution may be used as a fiber sizing to coat a mechanically strong underlying fiber during the fiber spinning process prior to take-up and subsequent use as a woven or non-woven product.

Example 4

Testing the Wound Dressings

It is contemplated that wound dressing comprising the polymer blends of the present invention can be tested for their efficacy in preventing or reducing the risk of infection of a wound site. Such testing methods are known by persons of ordinary skill in the art. One such protocol, for example, includes the following steps:

Fresh overnight suspension cultures of each of various medically important bacteria and fungi are coated onto the surface of trypticase soy agar, for bacteria, or Sabouraud's agar plates, for fungi. Circles, 5 mm in diameter, are cut from the silver-containing dressings and from control dressings that do not contain silver. The circles are placed on the surface of the cultured plates which are then incubated for 24-48 hours. Zones of inhibition are measured at the completion of the incubation phase. The diameter of the zones are measured.

All of the compositions and/or methods disclosed and claimed can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,859,719
U.S. Pat. No. 4,919,662
U.S. Pat. No. 5,326,567
U.S. Pat. No. 5,360,609
U.S. Pat. No. 5,631,300
U.S. Pat. No. 5,639,295
U.S. Pat. No. 5,650,446
U.S. Pat. No. 5,662,913
U.S. Pat. No. 5,668,185
U.S. Pat. No. 5,695,814
U.S. Pat. No. 5,705,092
U.S. Pat. No. 5,707,739
U.S. Pat. No. 5,709,870
U.S. Pat. No. 5,744,151
U.S. Pat. No. 5,863,548
U.S. Pat. No. 5,888,528
U.S. Pat. No. 5,914,120
U.S. Pat. No. 5,922,776
U.S. Pat. No. 6,046,243
U.S. Pat. No. 6,277,408
U.S. Pat. No. 6,605,304
U.S. Pat. No. 6,605,751
U.S. Pat. No. 6,669,981
Abuskhuana et al., *Polyhedron*, 23:1249, 2004.
Alice Ng, *Macromol.*, 27:3027-3033, 1994.
Avent et al., *J. Non-Crystalline Solids*, 328:31, 2003.
Belloni, *Rad. Phys. Chem.*, 67:291, 2003.
Bowler et al., *J. Burn Care and Rehab.*, 25(2):192, 2004.
Dowsett, Br. *J. Nursing*, 12(19):S44, 2003.
Engelmeyer et al., Biomaterials, 24, 2523 (2003).
Galeano et al., *Appl. Environ. Microbiol.*, 69(7):4329, 2003.
GB Appln. 2392913A
Han et al., *J. Environmental Health*, 66(4): 16, 2003.
Henglein, *J. Phys. Chem.*, 97:5457, 1993.
Holder et al., *Burns*, 29:445, 2003.
Iwasaki et al., Biomaterials, 24, 3599 (2003).
Jones et al., *Wound Repair Regen.*, 12(3):288, 2004.
Jose et al., *Chem. Commun.*, 2046, 2001.
Kang et al., *J. Membrane Sci.*, 236:163, 2004.
Kim et al., *J. Membrane Sci.*, 237:199, 2004.
Kim et al., *J. Poly. Sci.*, Part B: Poly. Phys., 42:2263, 2004.
Kim et al., *J. Poly. Sci.*: Part B: Poly. Phys., 42:232, 2004.
Kim et al., *Langmuir*, 17:5817, 2001.
Lee et al., *Angew. Chem. Int. Ed.*, 43:3053, 2004.
Lee et al., *Angew. Chem. Int. Ed.*, 43:3053, 2004.
Lee et al., *Coll. Polym. Sci.*, 283:295, 2004.
Lee et al., *Macromol.*, 21:954, 1988.
Lee et al., *Macromol.*, 21:954, 1988.
Mostafavi et al., *Chem. Phys. Lett.*, 167(3):193, 1990b.
Mostafavi et al., *Chem. Phys. Lett.*, 169(1-2):81, 1990a.
Mostafavi et al., *Chem. Phys. Lett.*, 218(1-2):115, 1994.
Mussini et al., *J. Electroanalytical Chem.*, 552:213, 2003.

Pappenfus et al., *Solid State Ionics*, 171:41, 2004.
Park et al., *J. Membrane Sci.*, 17:285, 2003.
Rodriguez et al., *Adv. Polym. Tech.*, 19(2):113, 2000.
Ruokolainen, *Macromol.*, 28:7779, 1995.
Shin et al., *Inorg. Chem.*, 42:2977, 2003.
Solymosi, *Zeitshrift fur Physikalische Chemie-Frankfurt*, 57(1-2) S: 1, 1968.
Troupis et al., *Appl. Catalysis B: Environ.*, 42:305, 2003.
Wellinghoff et al., *J. Poly. Sci.*, Part B: Poly. Phys., 29(2):247, 1991.
Xu et al., *Polymer*, 40:2239, 1999.
Yi et al., *Carbohydrate Polymers*, 53:425, 2003.
Young et al., *J. Appl. Microbiology*, 95: 54, 2003.
Zheng and Mi, *Polymer*, 44:1067, 2003.

What is claimed is:

1. A composition comprising:
    (a) a hydrophilic polymer comprising a polyvinylpyridine hydrophilic polymer and a chlorite anion;
    (b) a hydrophobic polymer comprising carboxylate substituted hydrophobic polymer; and
    (c) a silver ion present at a level of 0.01% to 9.9% by weight,
    wherein the silver ion is associated with a pyridine group of said polyvinylpyridine hydrophilic polymer and a negatively charged carboyxlate group of said carboxylate substituted hydrophobic polymer so as to form a molecular bridge between the hydrophilic polymer and the hydrophobic polymer; and wherein said chlorite anion oxidizes any silver metal formed from said silver ion to inhibit formation of silver metal clusters.

2. The composition of claim 1, wherein the association between the silver ion and the hydrophilic polymer or the hydrophobic polymer is characterized as an ionic bond, a covalent bond, or a co-ordinate bond.

3. The composition of claim 1, wherein the chlorite anion is associated with the hydrophilic polymer by an electrostatic interaction.

4. The composition of claim 1, wherein the chlorite anion is associated with a cation.

5. The composition of claim 1, wherein a cation, associated with said anion, is selected from the group consisting of $Na^+$, $K^+$, $Li^+$, $Cs^+$, $Rb^+$, a tetra-alkylammonium cation, and mixtures thereof.

6. The composition of claim 1, wherein the hydrophobic or hydrophilic polymer comprises an anionic group.

7. The composition of claim 6, wherein the anionic group is a —$COO^-$ group.

8. The composition of claim 1, wherein the hydrophilic or hydrophobic polymers are substituted with a quaternary nitrogen azaaromatic or aliphatic group, wherein the quaternary nitrogen in the azaaromatic or aliphatic group comprises an anion.

9. The composition of claim 8, wherein the anion is $Cl^-$.

10. The composition of claim 1, wherein the silver ion is obtained from $AgBF_4$, $AgPF_6$, $AgSO_3CF_3$, $AgClO_4$, $AgNO_3$, n-alkylArSO$_2$Ag, or n-alkylCOOAg.

11. The composition of claim 1, wherein the composition comprises between about 1% to about 10% by weight of chlorite ion.

12. The composition of claim 1, wherein the composition comprises between about 20% to about 80% by weight of hydrophilic polymer.

13. The composition of claim 1, wherein the compositions comprises between about 20% to about 80% by weight of a hydrophobic polymer.

14. The composition of claim 1, wherein the hydrophilic/hydrophobic polymer ratio is between 1/4 to about 4/1.

15. The composition of claim 1, wherein the composition is transparent.

16. The composition of claim 1, wherein the composition is a controlled release silver ion composition.

17. The composition of claim 1, wherein the composition is comprised on the surface of a medical device.

18. The composition of claim 17, wherein the medical device is selected from the group consisting of a scalpel, a tong, a retractor, and a glove.

19. The composition of claim 1, wherein the composition is comprised in a wound dressing.

20. The composition of claim 1, wherein the composition is a wound dressing.

21. The composition of claim 1, wherein the hydrophobic polymer is selected from the group consisting of alkyl acrylates, polymethylmethacrylate, polybenzylmethacrylate, polyphenylmethacrylate, and polyvinyl cinnamate; said polymer comprising partially neutralized carboxylic groups selected from the group consisting of acrylic acid monomer, methacrylic acid monomer, maleic acid, hydrolyzed anhydride monomer, substituted phthalic acid, hydrolyzed acid anhydride monomer, and hydrolyzed α-hydroxyacid ester so as to provide both acidic carboxylic groups and carboxylate anions.

22. The composition of claim 1, wherein the silver ion is photo-stable or thermo-stable.

23. The composition of claim 1, wherein the silver ion associates with said pyridine group of said polyvinylpyridine hydrophilic polymer through a metal co-ordination bond.

24. The composition of claim 1, wherein the silver ion bonds to an arene group of a styrene-acrylic acid copolymer through a d-π interaction.

25. The composition of claim 1, wherein said chlorite anion stabilizes the silver ion.

26. The composition of claim 1, wherein said chlorite anion minimizes coloring due to silver metal particles in the visible region spectrum.

27. The composition of claim 1, wherein said chlorite anion maximizes the availability of silver ion to act as a biocide.

* * * * *